United States Patent
Hereen et al.

(10) Patent No.: US 9,323,049 B2
(45) Date of Patent: Apr. 26, 2016

(54) FORWARD SCANNING OPTICAL PROBES WITH ONE OR MORE ROTATING COMPONENTS

(71) Applicant: ALCON RESEARCH, LTD., Fort Worth, TX (US)

(72) Inventors: Tammo Hereen, Alisa Viejo, CA (US); Mauricio Jochinsen, Fountain Valley, CA (US); Dean Y. Lin, Chino Hills, CA (US); Michael J. Papac, North Tustin, CA (US); Kambiz Parto, Laguna Hills, CA (US); Edouard G. Schmidtlin, Studio City, CA (US); Barry L. Wheatley, Oceanside, CA (US); Lingfeng Yu, Rancho Santa Margarita, CA (US)

(73) Assignee: Novartis AG (CH)

( * ) Notice: Subject to any disclaimer, the term of this patent is extended or adjusted under 35 U.S.C. 154(b) by 393 days.

(21) Appl. No.: 13/888,526

(22) Filed: May 7, 2013

(65) Prior Publication Data
US 2014/0333978 A1    Nov. 13, 2014

(51) Int. Cl.
G02B 26/08    (2006.01)
G02B 26/10    (2006.01)
A61B 5/00     (2006.01)

(52) U.S. Cl.
CPC ............ G02B 26/108 (2013.01); A61B 5/0062 (2013.01); *G02B 26/103* (2013.01)

(58) Field of Classification Search
CPC ............ G02B 27/4227; G02B 5/1828; A61B 1/00096; A61B 1/00064; A61B 1/00066; A61B 1/0098; A61B 1/00172; A61B 5/0066; A61B 5/6852

USPC ............ 359/210.2, 837, 211.2; 600/478, 129, 600/176, 182

See application file for complete search history.

(56) References Cited

U.S. PATENT DOCUMENTS

| 6,485,413 | B1 | 11/2002 | Boppart et al. |
| 7,261,687 | B2 * | 8/2007 | Yang .............................. 600/173 |
| 7,364,543 | B2 | 4/2008 | Yang et al. |
| 2010/0030031 | A1 * | 2/2010 | Goldfarb ............ A61B 1/00066 600/163 |

OTHER PUBLICATIONS

Yaqoob, Z., et al., "Methods and application areas of endoscopic optical coherence tomography", J. of Biomedical Optics, Nov./Dec. 2006, vol. 11(6), pp. 063001-1-0063001-19.

* cited by examiner

*Primary Examiner* — Euncha Cherry

(57) ABSTRACT

In certain embodiments, a scanning system comprises optical elements and a movement system. The optical elements comprise an optical fiber and a focusing element. The optical fiber transmits a light ray and has a fiber axis that extends to an imaginary fiber axis. The focusing element refracts the light ray and has a focusing element optical axis that is substantially aligned with the imaginary fiber axis. The movement system rotates the focusing element about the focusing element optical axis to scan the light ray. In other embodiments, a scanning system comprises optical elements and a movement system. The optical elements comprise an optical fiber, a focusing element, and a prism. The prism has a prism optical axis and receives the light ray from the focusing element. The movement system rotates the prism about the prism optical axis to scan the light ray.

10 Claims, 2 Drawing Sheets

FORWARD SCANNING OPTICAL PROBES WITH ONE OR MORE ROTATING COMPONENTS

TECHNICAL FIELD

The present disclosure relates generally to surgical devices, and more particularly to forward scanning optical probes.

BACKGROUND

Optical imaging techniques generate images of targets such as portions of a body, e.g., the interior of an eye. Examples of such techniques include interferometric imaging (e.g., optical coherence tomography (OCT)), spectroscopic imaging (e.g., fluorescence), Raman imaging, diffuse-wave optical imaging, and two-photon imaging techniques. Certain techniques, such as the interferometric imaging techniques, use a scanning system to scan a light ray across the target to image the target. Optical elements such as mirrors and lenses may be used to move the light ray.

BRIEF SUMMARY

In certain embodiments, a scanning system comprises optical elements and a movement system. The optical elements comprise an optical fiber and a focusing element. The optical fiber transmits a light ray and has a fiber axis that extends to an imaginary fiber axis. The focusing element refracts the light ray and has a focusing element optical axis that is substantially aligned with the imaginary fiber axis. The movement system rotates the focusing element about the focusing element optical axis to scan the light ray. In other embodiments, a scanning system comprises optical elements and a movement system. The optical elements comprise an optical fiber, a focusing element, and a prism. The prism has a prism optical axis and receives the light ray from the focusing element. The movement system rotates the prism about the prism optical axis to scan the light ray.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
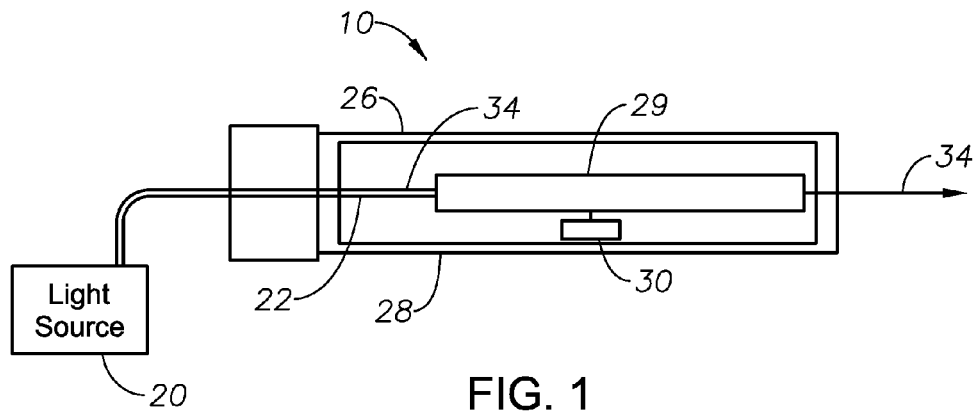
FIG. 1 illustrates an example of a probe with a scanning system that scans according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a probe 10 with a scanning system 28 that scans according to certain embodiments. In the illustrated embodiment, probe 10 includes a light source 20 and a housing 26 coupled as shown. A scanning system 28 is disposed within housing 26. Scanning system 28 include one or more optical elements 29 (including optical fiber 22) and a movement system 30. In an example of operation, light source 20 provides a light ray 34 that is transmitted through optical fiber 22 to other optical elements 29. Movement system 30 moves one or more of the optical elements 29 in order to output a scanning light ray 34.

Light source 20 may be a laser that generates light. Examples of laser include gas lasers, dye lasers, metal vapor lasers, solid state lasers, semiconductor lasers, fiber lasers, and supercontinuum lasers. The light may have any suitable spectral range, e.g., 750 nm to 950 nm.

Housing 26 (e.g., a cannula) may have any suitable shape and size. The housing may have a tubular (or cylindrical) shape with any suitable length and diameter, such as a length in the range of one to two inches, an outer diameter (OD) in the range of 0.05 to 0.02 inches, and an inner diameter (ID) in the range of 0.04 to 0.01 inches (but of course can be larger or smaller). For cannulas, the size may depend on the gauge (ga) of the cannula. For example, 20 ga cannulas may be approximately 0.0365" in OD and 0.031" in ID; 23 ga cannulas may be approximately 0.0255" in OD and 0.021" in ID; and 25 ga cannulas may be approximately 0.0205" in OD and 0.0156" in ID. This disclosure contemplates even smaller (higher gauge) cannulas.

Scanning system 28 receives light ray 34 and scans light ray 34 to output a scanning light ray 34. Scanning system 28 includes one or more optical elements 29 and movement system 30. An optical element 29 may be any suitable optical element that can reflect, refract, and/or diffract light. Examples of optical elements include optical fibers (e.g., optical fiber 22), lenses, prisms, mirrors, or other elements that can reflect, refract, and/or diffract light. Certain optical elements, such as focusing elements, operate to focus light. Examples of focusing elements include a gradient-index (GRIN) lens, an aspheric lens or other lens, and a ball lens.

An optical element 29 has an optical axis. For example, optical fiber 22 has a fiber axis. To aid in the description of relative movement among optical elements 29, the optical axis of an optical element 29 may be regarded as extending past the physical boundaries of the element as an imaginary axis. For example, the fiber axis may be described as extending to an imaginary fiber axis. In certain embodiments, an optical axis of an optical element 29 may have specific features. For example, light rays passing through the optical axis of a GRIN lens may be output with zero degrees of refraction.

Optical fiber is generally a transparent fiber that operates as a waveguide to transmit light from a laser source 20. Optical fiber 22 may include an optically transmissive fiber core surrounded by a cladding material having a generally low index of refraction relative to the fiber core. Optical fiber 22 may comprise any suitable material, e.g., glass and/or plastic. Optical fiber 22 may include additional layers depending on the requirements of a particular application. Optical fiber 22 has a fiber axis that is typically the optical axis of the fiber core.

Movement system 30 may move an optical element 29 in any suitable manner. For example, the optical element may be translated, rotated about an axis, or orbited around an axis. A translational movement is generally linear motion. A rotational movement of an object is movement about an axis of the object. An orbital movement of an object is movement around an axis external to the object. A rotational or orbital movement may be any suitable number of degrees, e.g., 360° or less, such as approximately 90°, 180°, 270°, or 360°. Movement system 30 may move an optical element in a closed path in which the starting point of the path substantially coincides with the ending point. Alternatively, movement system 30 may move (translate, rotate, or orbit) an optical element in one direction and then reverse directions to move in the opposite direction.

Movement system 30 may move an optical element 29 using any suitable movement mechanism. As an example, an electric motor (e.g., a piezoelectric motor) may be used to move an optical element 29. As another example, electrostatic plates may be used to move an optical element 29 treated with a metalized material. As yet another example, a pneumatic drive with appropriate mechanism can be used to move an optical element 29. In certain embodiments, movement system 30 may be controlled by one or more computer readable media encoded with a computer program.

FIGS. 2 through 5 illustrate examples of scanning systems 28 that include optical elements 29 and a moving system 30. The optical axes of one or more of the optical elements 29 may be aligned with each other. Moving system 30 rotates one or more of the optical elements 29 to scan light ray 34. Any suitable rotational speed may be used, e.g., a speed in the range of 300 rotations per minute (rpm) to 6000 rpm. Moving system 30 may be coupled to one or more of the optical elements 29 that it rotates.

Figure 2:
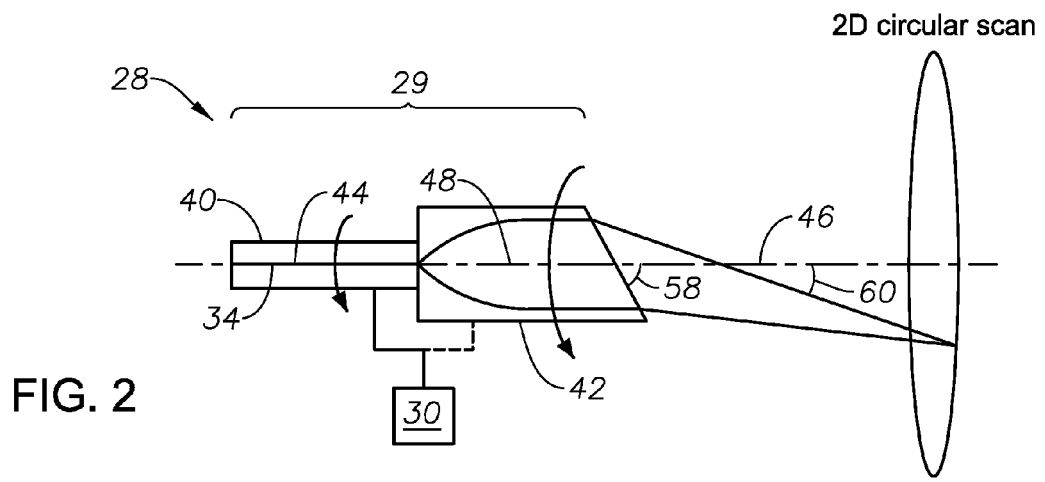
FIG. 2 illustrates an example of a scanning system that scans according to certain embodiments.
Figure 3:
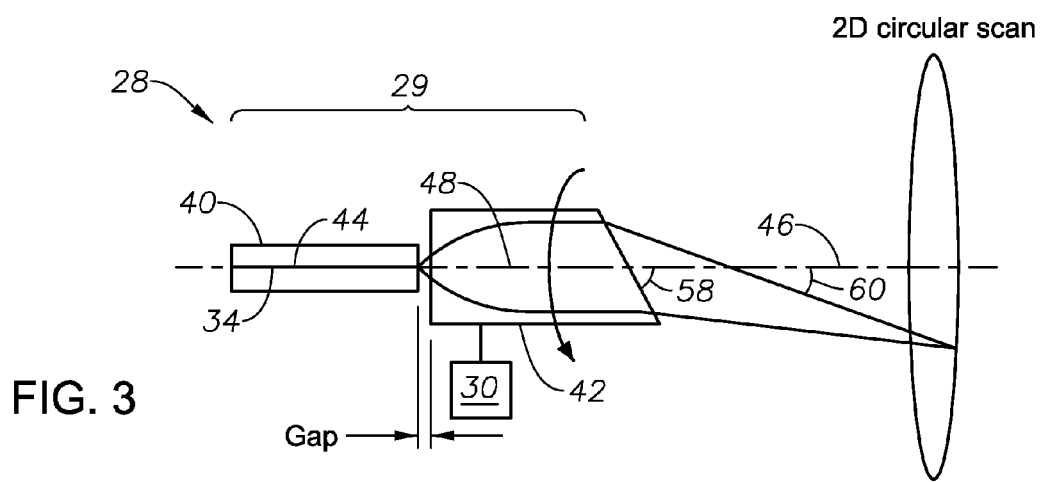
FIG. 3 illustrates an example of a scanning system that scans according to certain embodiments.

FIGS. 2 and 3 have optical elements 29 that include optical fiber 40 and GRIN lens 42 (or other focusing element). GRIN lens optical axis 48 may be substantially aligned with imaginary fiber axis 46. In certain embodiments, GRIN lens 42 may have a distal end surface that has an angle 58 relative to GRIN lens optical axis 48 such that light ray 34 exits GRIN lens 42 at an angle 60. Angle 58 may have any suitable value, e.g., a value in the range of 10° to 30°, such as 15° to 25°.

In FIG. 2, moving system 30 rotates both optical fiber 40 and GRIN lens 42 and can be coupled to optical fiber 40 and/or GRIN lens 42. Optical fiber 40 may be coupled to GRIN lens 42. In FIG. 3, moving system 30 is coupled to and rotates only GRIN lens 42. There may be a gap between optical fiber 40 and GRIN lens 42 such that GRIN lens 42 can rotate without interference from optical fiber 40.

Figure 4:
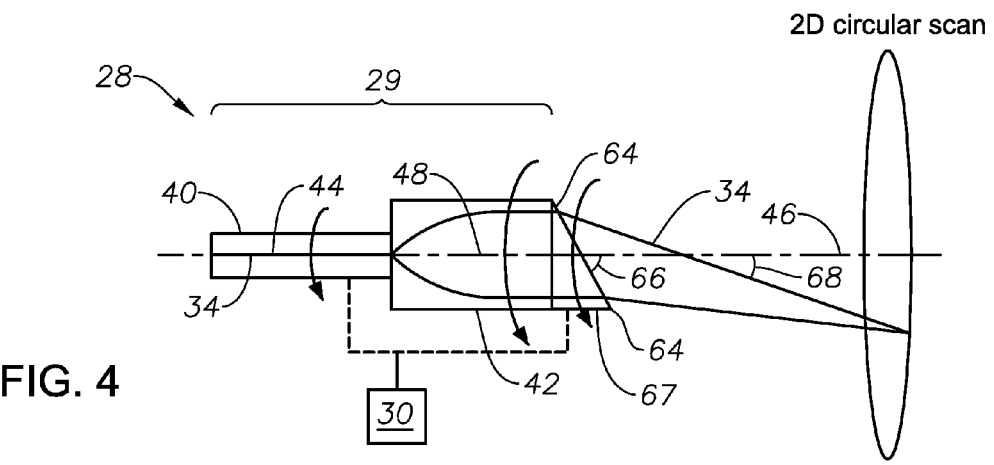
FIG. 4 illustrates an example of a scanning system that scans according to certain embodiments.
Figure 5:
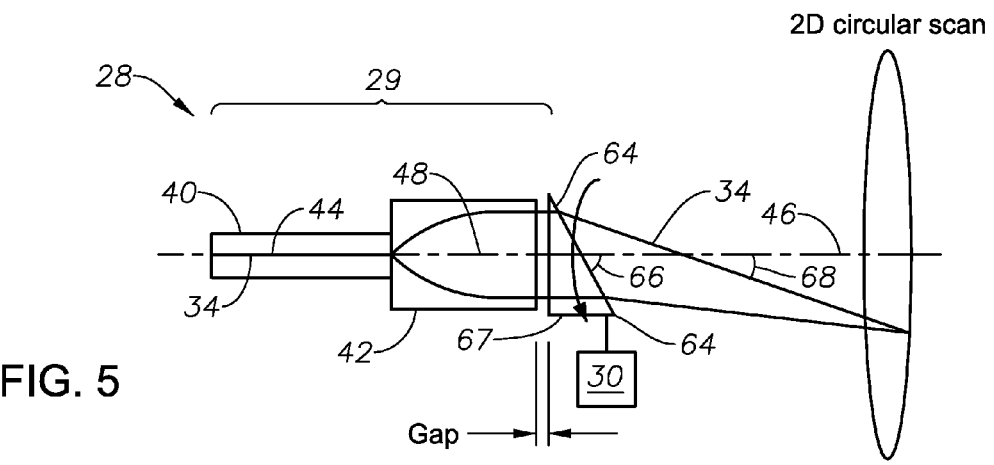
FIG. 5 illustrates an example of a scanning system that scans according to certain embodiments.

FIGS. 4 and 5 have optical elements 29 that include optical fiber 40, GRIN lens 42 (or other focusing element), and a prism 64. In certain embodiments, prism 64 may have a distal end surface that has an angle 66 relative to prism optical axis 67 such that light ray 34 exits prism 64 at an angle 68. GRIN lens optical axis 48 and/or prism optical axis 67 may be substantially aligned with imaginary fiber axis 46. Angle 66 may have any suitable value, e.g., a value in the range of 10° to 30°, such as 15° to 25°.

In FIG. 4, moving system 30 rotates optical fiber 40, GRIN lens 42, and prism 64, and can be coupled to optical fiber 40, GRIN lens 42, and/or prism 64 each other GRIN lens 42. In FIG. 5, moving system 30 is coupled to and rotates only prism 64. There may be a gap between GRIN lens 42 and prism 64 such that prism 64 can rotate without interference from GRIN lens 42.

A component (e.g., scanning system 28 and/or movement system 30) of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments (e.g., control of scanning of light ray 34) may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A scanning system comprising:
   a plurality of optical elements comprising:
   an optical fiber having a fiber axis, the optical fiber configured to transmit a light ray, the fiber axis extending to an imaginary fiber axis;
   a focusing element having a focusing element optical axis that is substantially aligned with the imaginary fiber axis, the focusing element configured to receive the light ray from the optical fiber and refract the light ray; and
   a prism having a prism optical axis substantially aligned with the imaginary fiber axis, the prism configured to receive the light ray from the focusing element; and
   a movement system coupled to at least the prism and configured to:
   rotate the prism separately from the focusing element about the prism optical axis to scan the light ray.

2. The system of claim 1, the movement system further configured to:
   rotate the focusing element about the focusing element optical axis along with the prism.

3. The system of claim 1, the movement system further configured to:
   rotate the focusing element about the focusing element optical axis and the optical fiber about the fiber axis along with the prism.

4. The system of claim 1, wherein the focusing element is one of the following: a gradient-index (GRIN) lens, an aspheric lens, or a ball lens.

5. A scanning method comprising:
   transmitting a light ray through an optical fiber having a fiber axis, the fiber axis extending to an imaginary fiber axis;
   transmitting the light ray through a focusing element having a focusing element optical axis that is substantially aligned with the imaginary fiber axis, the focusing element configured to receive the light ray from the optical fiber and refract the light ray;
   initiating movement of a prism having a prism optical axis that is substantially aligned with the imaginary fiber axis, the prism configured to receive the light ray from the focusing element and refract the light ray; and
   rotating the prism separately from the focusing element about the prism optical axis to scan the light ray.

6. The method of claim 5, further comprising:
   rotating the focusing element about the focusing element optical axis along with the prism.

7. The method of claim 5, further comprising:
   rotating the focusing element about the focusing element optical axis and the optical fiber about the fiber axis along with the prism.

8. The method of claim 5, wherein the focusing element is one of the following: a gradient-index (GRIN) lens, an aspheric lens, or a ball lens.

9. The system of claim 1, wherein there is a gap between the prism and the focusing element.

10. The method of claim 5, wherein there is a gap between the prism and the focusing element.

* * * * *